United States Patent [19]

Hinnenkamp et al.

[11] Patent Number: 5,817,869
[45] Date of Patent: Oct. 6, 1998

[54] USE OF PENTAVALENT GROUP VA OXIDES IN ACETIC ACID PROCESSING

[75] Inventors: James A. Hinnenkamp; Noel Hallinan, both of Cincinnati, Ohio

[73] Assignee: Quantum Chemical Corporation, Cincinnati, Ohio

[21] Appl. No.: 720,831

[22] Filed: Oct. 3, 1996

Related U.S. Application Data

[63] Continuation-in-part of Ser. No. 538,561, Oct. 3, 1995.
[51] Int. Cl.$^6$ .............................. C07C 51/12; C07C 51/10
[52] U.S. Cl. ............................................. 562/519; 562/517
[58] Field of Search ...................... 562/519, 517

[56] References Cited

U.S. PATENT DOCUMENTS

| | | | |
|---|---|---|---|
| 3,818,060 | 6/1974 | Forster et al. | 554/129 |
| 3,939,219 | 2/1976 | Wilkinson | 585/275 |
| 4,102,920 | 7/1978 | Bartish | 562/519 |
| 4,190,729 | 2/1980 | Forster | 560/232 |
| 4,194,056 | 3/1980 | Antoniades | 562/516 |
| 4,562,284 | 12/1985 | Drent | 562/406 |
| 4,927,967 | 5/1990 | Wegmen | 562/607 |
| 5,001,259 | 3/1991 | Smith et al. | 562/519 |
| 5,003,104 | 3/1991 | Paulik et al. | 562/517 |
| 5,026,908 | 6/1991 | Smith et al. | 562/519 |
| 5,144,068 | 9/1992 | Smith et al. | 562/519 |
| 5,189,214 | 2/1993 | Chen et al. | 562/519 |
| 5,214,203 | 5/1993 | Koyama et al. | 562/519 |
| 5,281,751 | 1/1994 | Schreck | 562/519 |
| 5,391,821 | 2/1995 | Koyama et al. | 562/519 |
| 5,416,237 | 5/1995 | Aubigne et al. | 562/519 |

FOREIGN PATENT DOCUMENTS

| | | |
|---|---|---|
| 0 031 606 | 7/1981 | European Pat. Off. . |
| 0 072 055 | 2/1983 | European Pat. Off. . |
| 0 097 978 | 1/1984 | European Pat. Off. . |
| 0 114 703 | 8/1984 | European Pat. Off. . |
| 1 233 121 | 5/1971 | United Kingdom . |
| 1 326 014 | 8/1973 | United Kingdom . |

*Primary Examiner*—Paul J. Killos
*Assistant Examiner*—Rosalynd Keys
*Attorney, Agent, or Firm*—Scully, Scott, Murphy & Presser

[57] ABSTRACT

Methanol is converted to acetic acid by reaction with carbon monoxide in the presence of an carbonylation system which comprises a rhodium catalyst component and a liquid reaction medium containing acetic acid, methyl iodide, methyl acetate, and at least one pentavalent Group VA oxide and water in specific concentrations. The present carbonylation system not only increases the yields and reaction rates but also serves to stabilize the rhodium catalyst component in an active form.

24 Claims, 8 Drawing Sheets

USE OF PENTAVALENT GROUP VA OXIDES IN ACETIC ACID PROCESSING

CROSS-REFERENCE TO RELATED APPLICATION

This is a continuation-in-part of application Ser. No. 08/538,561, filed Oct. 3, 1995.

FIELD OF THE INVENTION

The present invention relates to a process for the production of acetic acid by carbonylation of methanol or its derivatives, such as methyl acetate or methyl iodide, with carbon monoxide in the presence of a rhodium-containing catalyst system. More specifically, the present invention is directed to the addition of specific amounts of one or more defined pentavalent Group VA oxides to a liquid carbonylation reaction medium having a select range of externally added water therein, the practice of the invention leading to unexpectedly high catalyst productivity and stability. The present invention further permits the elimination of alkali metal halides, such as lithium iodide as commonly used heretofore to stabilize and promote acetic acid carbonylation systems, from the same.

BACKGROUND OF THE INVENTION

Production methods for acetic acid are ever the subject of intense scrutiny given the commercial importance of this commodity. While various techniques exist to manufacture acetic acid on a large scale, those that involve carbonylation have attracted much attention given, among other reasons, the simplicity and ready availability of the primary reactants—namely, carbon monoxide and methanol—and the overall effectiveness of the carbonylation process to produce the acid product. Although carbonylation has become a preferred route to make acetic acid, there are nevertheless countervailing considerations which affect implementation of the same: the underlying reaction chemistry is intricate, involving a multiplicity of interrelated reactions, by-products and equilibria—all of which must be properly balanced, one against the other, to make the process practicable; and the catalyst systems required for carbonylation are generally complex, comprising rhodium and the like, and expensive.

Moreover, carbonylation catalyst systems are extraordinarily sensitive to changes in any number of reaction parameters which, in turn, adversely affect catalyst stability and activity.

Efforts to advance carbonylation processing have taken various paths, one of which being the deliberate addition of water to the reaction media. Water, in the ordinary course of some of the more common carbonylation schemes, is generated in situ as a natural by-product of reaction. For example, in carbonylation reactions wherein methanol is carbonylated via carbon monoxide, measurable amounts of water are formed in consequence of the equilibrium that exists between acetic acid and methyl acetate. It was found that adventitiously supplied water sped up the rate of reaction by which acetic acid was produced. However, it was found that too much externally added water either failed to further favorably affect the reaction rate or created other problems in processing, particularly in the area of product recovery. Commercially, these divergent considerations have been reconciled on an economic basis with the result that carbonylation processes today typically employ up to about 14% water by weight in the reaction mix.

Notwithstanding the improvements in carbonylation that have been attained through such processing, the self-limiting aspects of the same have led to the exploration of other ways to enhance productivity. In particular, attention has been directed to decreasing the amount of added water as much as possible, which in turn facilitates product recovery, while concurrently maintaining benefit of a reaction rate associated with higher water concentrations. Efforts in this regard have included the incorporation of various additives to the carbonylation system; the predominant ones being alkali metal halides, such as lithium iodide. Lithium iodide has been reportedly used as an additive in conjunction with so-called low water carbonylation technology to positively affect reaction rates and yields. Representative of such developments are: U.S. Pat. Nos. 5,214,203; 5,391,821; 5,003,104; 5,001,259; 5,026,908; 5,144,068; 5,281,751 and 5,416,237.

While the introduction of alkali metal halides such as lithium iodide into low water carbonylation systems for the production of acetic acid have enabled reductions in water content without attendant decreases in reaction rate, the high concentration of these materials are suspected of promoting stress crack corrosion of the reactor vessels in which they are used.

Insofar as Group VA compounds are concerned, the use of various of the same in a variety of contexts is known. These processes, however, either make no meaningful distinction between the use of trivalent Group VA compounds and pentavalent Group VA compounds and/or are directed to processes recognizably different from low water carbonylation of methanol to form acetic acid. Thus, for example, U.S. Pat. No. 3,939,219 and U.K. 1,326,014 disclose the use of trivalent organo-phosphorous, organo-arsenic, and organo-antimony compounds, as well as pentavalent phosphine oxides, as donor ligands for the stabilization of a catalyst solution where a strong acid, such as fluoroboric acid, is used. In the sole example relating to acetic acid synthesis, methanol is carbonylated to acetic acid and methyl acetate using triphenyl phosphine, along with a rhodium compound and fluoroboric acid.

Similarly, EP 0031606 and EP 0072055 disclose processes for the co-production of carboxylic acids and carboxylic acid esters using ruthenium and a further Group VIII metal compound. Among the compounds described as capable of coordinating with the Group VIII metal moieties are organo-phosphorous, organo-arsenic, organo-antimony, organo-nitrogen, organo-sulphur and organo-oxygen compounds. Specific compounds include trivalent phosphines and, by formula, pentavalent phosphine oxides.

Those processes that focus on the use of pentavalent Group VA compounds or otherwise distinguish the same from the trivalent species include EP 0097978, which describes a process for the co-production of carboxylic acids and carboxylic acids having an additional carbon atom. Promoters suitable for the process are principally limited to oxides of amines, phosphines, arsines and stilbines and the co-reaction is specifically related as having to be carried out under virtually anhydrous conditions. U.S. Pat. No. 3,818,060 expressly acknowledges a preference for pentavalent Group VA derivatives of phosphorous, arsenic, antimony, nitrogen and bismuth over trivalent derivatives of Group VA elements. But the derivatives are used as an adjunct with Group VIII metals to hydrocarboxylate unsaturated compounds to form higher carboxylic acids, such as ethylene to propionic acid, not to produce acetic acid.

U.S. Pat. No. 4,190,729 also discloses the use of pentavalent phosphorous compounds, such as phosphine oxides, but does so in conjunction with a cobalt catalyst and high pressure so to carbonylate methanol with carbon monoxide to form ethanol, acetaldehyde and methyl acetate. The use of extraneous water is not described, and acetic acid is disclosed as being produced in only minor amounts.

Lastly, EP 0114703 relates a process for the preparation of carboxylic acids and/or esters by carbonylation of alcohols using a rhodium catalyst, an iodide and/or bromide source and a promoter. Compounds contemplated as promoters in the process of EP 0114703 include oxides, sulphides or selenides of secondary and tertiary phosphines, arsines and stilbines. In the examples provided, triphenylphosphine oxide is used as the promoter in the formation of acetic acid, the reactions exemplified being conducted under anhydrous conditions. And while the presence of water in the reaction mixture is elsewhere mentioned in EP 0114703, the context is recognizably consistent with the presence of in situ generated water that is otherwise known to attend anhydrous processing. EP 0114703 is thus removed from low water carbonylation processes in the first instance, and is silent in regard to choosing optimal water ranges and promoters for such processes.

There is thus a continuing need in the art to develop a low water carbonylation process for the production of acetic acid that eliminates the need for alkali metal halides and concurrently permits a reduction in added water content, all while maintaining high levels of catalyst productivity and stability.

SUMMARY OF THE INVENTION

The present invention provides a low water process for the carbonylation of methanol with carbon monoxide to produce acetic acid using a rhodium-based catalyst which satisfies the foregoing criteria. It has been found in this regard that when certain oxides of pentavalent Group VA compounds are employed in concert with a specific range of externally-added water in a low water carbonylation process, the need for alkali metal halides is surprisingly eliminated and a level of catalyst productivity more commonly associated with a higher water content unexpectedly manifests along with improved catalyst stability.

Specifically, the present invention involves introducing into a carbonylation system, as hereinafter defined, at least one pentavalent Group VA oxide of the formula: $R_3M=O$, wherein M is an element from Group VA of the Periodic Table of Elements, such as N, P, As, Sb or Bi; and each R is independently a substituted or unsubstituted alkyl, aryl, aralkyl or alkaryl wherein any of which substituents of the carbon chains may be straight or branched or both. The pentavalent Group VA oxide is introduced into the carbonylation system in an amount such that its concentration relative to rhodium is greater than about 60:1.

The practice of the invention further comprises introducing water to the carbonylation system at an amount of from about 4 to about 12 weight % (which corresponds to a molarity of water of from about 2.5 to about 7.5M) based on the total amount of the carbonylation system, inclusive of the pentavalent Group VA oxide(s). More preferably, the concentration of water is from about 4 to about 11 weight % which corresponds to a molarity of about 3 to about 7M; more preferably, about 4 to about 9 weight %.

DETAILED DESCRIPTION OF THE PRESENT INVENTION

Figure 1A:
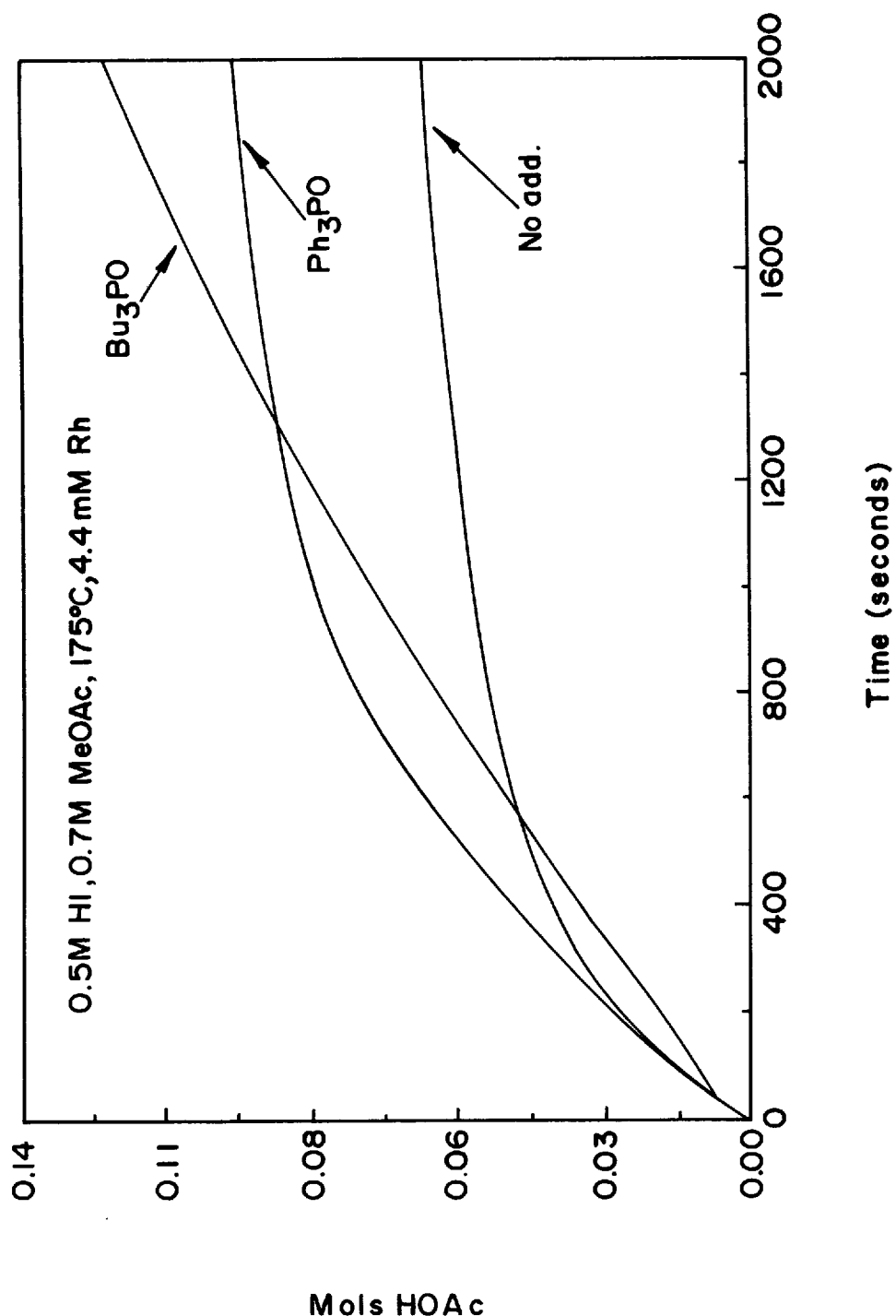
FIGS. 1(a) and (b) represent graphs of the overall rate (a) and initial rate (b) of HOAc production vs. time using the various carbonylation catalyst additives indicated in Examples 1 and 2.

In accordance with the present invention, improved catalyst stability, as well as improved yields and reaction rates, can be obtained by introducing at least one pentavalent Group VA oxide, as defined hereinbelow, to a carbonylation system, said carbonylation system comprising a rhodium-containing component and a liquid reaction medium, which reaction medium generally contains acetic acid, methyl iodide, and methyl acetate. In the practice of the invention, the amount of said pentavalent Group VA oxide is such that its concentration to rhodium is greater than about 60:1. Preferably, the concentration of the pentavalent Group VA oxide to rhodium is from about 60:1 to about 500:1.

Typically in the instant invention, from about 0.2 to about 3M pentavalent Group VA oxide is present in the liquid reaction medium. More preferably, from about 0.4 to about 1.5M pentavalent Group VA oxide is present in the liquid reaction medium.

Pentavalent Group VA oxides contemplated by the instant invention have the formula:

$$R_3M=O$$

wherein M is an element from Group VA of the Periodic Table of Elements such as N, P, As, Sb or Bi; and each R is independently a substituted or unsubstituted alkyl, aryl, aralkyl, or alkaryl wherein any of which substituents of the carbon chains may be straight or branched or both.

As employed herein, the alkyl groups, singly or in combination with other groups, contain up to 12 carbon atoms which may be in the normal or branched configuration, including methyl, ethyl, propyl, isopropyl, butyl, isobutyl, t-butyl, amyl, pentyl, hexyl, octyl and the like. The preferred alkyl groups contain 1 to 8 carbon atoms.

The aryl groups are aromatic rings containing from 6 to 14 carbon atoms. Examples or aryl groups include phenyl, α-naphthyl and β-naphthyl, with phenyl being highly preferred.

The aralkyl groups, singly or in combination with other groups, contain up to 16 carbon atoms with each aryl group containing from 6 to 10 carbon atoms and each alkyl group containing up to 6 carbon atoms which may be in the normal or branched configuration. Preferably, each aryl group contains 6 carbon atoms and each alkyl group contains 1 to 3 carbon atoms.

The alkaryl groups, singly or in combination with other groups, contain up to 16 carbon atoms with each alkyl group containing up to 8 carbon atoms which may be in the normal or branched configuration, and each aryl group containing from 6 to 10 carbon atoms. Preferably, each alkyl group contains 6 carbon atoms.

As indicated herein each R group may be substituted or unsubstituted. When R is substituted, it is typically substituted with an alkyl group as defined hereinabove R may also be substituted with other substituents such as halogen, hydroxy, nitro, amino and the like.

In a preferred embodiment of the instant invention, M is phosphorus, and each R is independently either a substituted or unsubstituted alkyl or aryl containing from about 1 to about 6 carbon atoms.

Specific examples of especially preferred pentavalent Group VA oxides that can be used in the instant invention include, but are not limited to, triethylphosphine oxide, tributylphosphine oxide, tripentylphosphine oxide, diphenylmethylphosphine oxide and triphenylphosphine oxide, with tributylphosphine oxide and triphenylphosphine oxide being more preferred. It should be noted that tributylphosphine oxide is most highly preferred when catalyst stability is the desirable end result and triphenylphosphine oxide is most highly preferred when enhanced rate is the desired goal.

Mixtures of pentavalent Group VA oxides having the foregoing formula are also contemplated within the practice of the present invention.

Without being bound to any particular theory, it is postulated that the quantity of the specific pentavalent Group VA oxides employed in the instant invention, as within the strictures of the aforementioned concentration ranges, will maintain the rhodium catalyst in an active form, thus preventing any significant precipitation of the rhodium catalyst during the carbonylation process. By maintaining the rhodium catalyst in an active form, less rhodium is utilized in the carbonylation process. As is well known to those skilled in the art, the active form of rhodium for methanol carbonylations is one which has an oxidation state of I whereas the inactive form of rhodium has an oxidation state of III.

As those skilled in the art are also aware, rhodium is an expensive transition metal; and reducing the amount of rhodium used in the carbonylation process thus reduces the overall cost of the carbonylation process.

The rhodium-containing component of catalyst systems to which the instant invention has application includes those that are known and used in the prior art for carbonylation purposes—especially those used in carbonylation to produce acetic acid.

The rhodium-containing component of carbonylation systems to which the present invention has application may be provided by introduction into the reaction zone of a suitable compound of rhodium or of rhodium metal. Among the materials which may be charged into the reaction zone in this regard are, without limitation, rhodium metal, rhodium salts, rhodium oxides, rhodium acetates, organo-rhodium compounds, coordination compounds of rhodium and the like. Mixtures of such rhodium sources are also contemplated herein.

Specific examples of rhodium-containing components of catalyst systems to which the present invention has application include, without limitation: $RhCl_3$; $RhBr_3$; $RhI_3$; $RhCl_3 \cdot 3H_2O$; $RhBr_3 \cdot 3H_2O$; $RhI_3 \cdot 3H_2O$; $Rh_2(CO)_4Cl_2$; $Rh_2(CO)_4Br_2$; $Rh_2(CO)_4I_2$; $Rh_2(CO)_8$; $Rh(CH_3CO_2)_2$; $Rh(CH_3CO_2)_3$; $Rh[(C_6H_5)_3P]_2(CO)I$; $Rh[(C_6H_5P)]_2(CO)Cl$; Rh metal; $Rh(NO_3)_3$; $Rh(SnCl_3)[(C_6H_5)_3P]_2$; $RhCl(CO)[(C_6H_5)_3As]_2$; $RhI(CO)[(C_6H_5)_3Sb]_2$; $[Y][Rh(CO)_2X_2]$ wherein $X=Cl^-$, $Br^-$ or $I^-$; and Y is a cation selected from the group consisting of positive ions from Group IA of the Periodic Table of Elements, such as H, Li, Na, K, or Y is a quaternary ion of N, As or P; $Rh[(C_6H_5)_3P]_2(CO)Br$; $Rh[(n-C_4H_9)_3P]_2(CO)Br$; $Rh[(n-C_4H_9)_3P]_2(CO)I$; $RhBr[(C_6H_5)_3P]_3$; $RhI[(C_6H_5)_3P]_3$; $RhCl[(C_6H_5)_3P]_3$; $RhCl[(C_6H_5)_3P]_3H_2$; $[(C_6H_5)_3P]_3Rh(CO)H$; $Rh_2O_3$; $[Rh(C_3H_4)_2Cl]_2$; $K_4Rh_2Cl_2(SnCl_2)_4$; $K_4Rh_2Br_2(SnBr_3)_4$; $[H][Rh(CO)_2I_2]$; $K_4Rh_2I_2(SnI_2)_4$ and the like.

The present invention has preferred application to systems wherein the rhodium-containing component is $Rh_2(CO)_4I_2$, $Rh_2(CO)_4Br_2$, $Rh_2(CO)_4Cl_2$, $Rh(CH_3CO_2)_2$, $Rh(CH_3CO_2)_3$ or $[H][Rh(CO)_2I_2]$, with $[H][Rh(CO)_2I_2]$, $Rh(CH_3CO_2)_2$ and $Rh(CH_3CO_2)_3$ being most preferred.

In practice, the rhodium concentration can vary over a wide range, although it is recognized that enough metal must be present to achieve reasonable carbonylation reaction rates; excess metal on the other hand may on occasion result in undesired by-product formation. The typical rhodium concentration in those carbonylation systems to which the instant invention has application is from about 200 to about 1200 ppm (about $2 \times 10^{-3}$ to about $13 \times 10^{-3}$M). More preferably, the rhodium concentration is from about 400 to about 1000 ppm (about $4 \times 10^{-3}$ to about $10 \times 10^{-3}$M). The amount of rhodium used is not a critical feature and higher concentrations are acceptable, subject to economic considerations.

As indicated above, the carbonylation system to which the instant invention has application includes a rhodium-containing component, as described above, and a liquid reaction medium which generally comprises methyl acetate, methyl iodide and acetic acid.

In the practice of the invention, water is deliberately introduced in select amounts into the carbonylation system. The concentration of water present in carbonylation system to which the instant invention relates is from about 4 to about 12 weight % (about 2.5 to about 7.5M) based on total weight of the carbonylation system inclusive of the pentavalent Group VA oxides. More preferably, the concentration of water present in the carbonylation system is from about 4 to about 11 weight % (about 2.7 to about 7M); most preferably about 4 to about 9 weight % water is present.

In accordance with the present invention, the ratio of water to rhodium employed in the present is from about 4000:1 to about 200:1. More preferably, the ratio of water to rhodium employed in the present invention is from about 1750:1 to about 270:1.

Another component of the liquid reaction medium aspect of the carbonylation system to which the instant invention pertains is methyl acetate, which can be charged into the reactor or can be formed in-situ in an amount of from about 0.5 to about 10 weight % based on the total weight of the liquid reaction medium. The foregoing weight % range of methyl acetate corresponds to a methyl acetate molarity of from about 0.07 to about 1.4M. More preferably, the concentration of methyl acetate employed in the process of the present invention is from about 1 to about 8 weight % (about 0.14 to about 1.1M).

The corresponding ratio of methyl acetate to rhodium employed in the present invention is from about 700:1 to about 5:1. More preferably, the ratio of methyl acetate to rhodium is from about 275:1 to 14:1.

A third component of the subject liquid reaction medium is methyl iodide ($CH_3I$), which can be added directly to or can be formed in-situ by using HI. Typically, the concentration of $CH_3I$ employed in the instant invention is from about 0.6 to about 36 weight % (0.05 to about 3M). More preferably, the concentration of $CH_3I$ employed in the instant invention is from about 3.6 to about 24 weight %

(about 0.3 to about 2.0M). When HI is employed, it is generally present in a concentration of from about 0.6 to about 23 weight % (0.05 to about 2.0M). More preferably, the concentration of HI is from about 2.3 to about 11.6 weight % (0.2 to about 1.0M).

The fourth component of the liquid reaction medium is acetic acid (HOAc), which is typically present in the reactor in an amount of from about 20 to about 80 weight %. The corresponding molarity range being from about 3 to about 12M. More preferably, the amount of acetic acid that is charged into the reactor is from about 35 to about 65 weight % (about 5 to about 10M).

Hydrogen may also be fed into the reactor to increase the overall rate of the carbonylation process. In this embodiment, improved carbonylation efficiency can be obtained when the addition of hydrogen to the reactor maintains a concentration of from about 0.1 to about 5 mole % $H_2$, based on the total number of moles of CO in the reactor. The preferred hydrogen addition is sufficient to maintain a concentration of from about 0.5 to about 3 mole % $H_2$ in the reactor. Hydrogen may be added to the reactor either as a separate stream or together with carbon monoxide; make-up amounts can be introduced in the same manner, as needed, to maintain the hydrogen concentration at the levels defined hereinabove.

In addition to the components mentioned hereinabove, a solvent or diluent may, optionally, be present. If a solvent or diluent is employed it is preferred that they be inert. The term "inert" as used herein means that the solvent or diluent does not interfere with the reaction to any significant extent. Illustrative examples of solvents or diluents that may optionally be used include, but are not limited to, 1,4-dioxane, polyethylene glycol diethers or diesters, diphenyl ether, sulfolane, toluene, carboxylic acids and the like. Mixtures of these inert solvents or diluents may also be present. Generally, the reaction is carried in the absence of any solvent or diluent other than those required to introduce reactants or catalyst components into the reactor.

The carbonylation process of the present invention, which does not evince any induction time for carbonylation, can be carried out either in a batch or continuous mode. When operating in a continuous mode, the reaction system hardware usually comprises (a) a liquid phase carbonylation reactor, (b) a so-called "flasher", and (c) a methyl iodide-acetic acid splitter column. Other reaction zones or distillation columns may be present. Such hardware and the operation thereof are well known in the art. When operating in a continuous mode, the carbonylation reactor is typically a stirred autoclave within which the concentration of the reactants are maintained automatically at a constant level.

The carbonylation processes to which the instant invention relates is, for either mode, typically conducted under a pressure of from about 200 to about 1200 psig. More preferably, the carbonylation is conducted under a pressure of about 300 to about 600 psig.

The carbonylation processes to which the present invention relates is typically carried out at a temperature of from about 160° C. to about 220° C. More preferably, carbonylation is carried out at a temperature of from about 170° C. to about 200° C.

In practice, carbonylation reaction time varies, depending upon reaction parameters, reactor size and charge, and the individual components employed.

The experiments and examples detailed hereinbelow were carried out in a batch mode using a Hastelloy (trademark) C-276 stirred 300 ml autoclave. The reactor head was equipped with attachments for cooling coils, thermocouples and dip tubes for sample exit and return. Loss of vapor to the vapor stack was minimized by two in-series condensers.

The liquid reaction components, minus the catalyst, were then charged to the reactor. After leak testing with nitrogen and purging with CO, the reactor and its contents were heated to the desired temperature at a CO pressure of 100–200 psig with agitation.

The reaction was then started by injecting a chosen amount of a rhodium-containing catalyst into the reactor, following which the pressure of the reactor was raised to 400 psig. The reaction was allowed to proceed at constant pressure, which was maintained by feeding CO from a high pressure reservoir via a regulator. The extent of the carbonylation reaction was measured by the pressure drop in the reservoir. The pressure drop was converted to the moles of CO reacted using the known reservoir volume. At appropriate time intervals, infrared spectra were recorded to determine the active Rh(I) content using a Nicolet (trademark) 20DX spectrometer and liquid samples were removed for gas chromatographic analysis.

The liquid samples were analyzed using a Varian (trademark) 3400 Gas Chromatograph fitted with a 60 m×0.32 mm Nukol (0.25 micron film) capillary column. Gases were analyzed on-line using a Carle (trademark) series 400 AGC by opening a gas sampling valve and allowing the Carle sample valve to purge with reactor gas.

As stated above, improved carbonylation rates, product yields, and catalyst stability are obtained in the instant invention by incorporating at least one pentavalent Group VA oxide, as defined above, conjointly with a select range of externally-supplied water into a carbonylation system as described hereinabove. Unlike prior art processes, no alkali metal halides, e.g., LiI, are required in the practice of the instant invention wherefrom improved rates, yields and stability are provided. Moreover, the improvements herein ascribed to the use of certain pentavalent Group VA oxides in tandem with defined water ranges are demonstrably superior to results obtained with prior art processes using additives, such as phosphines and phosphites.

The following examples are given to illustrate the scope of this invention. Because these examples are given for illustrative purposes only, the present invention should not be limited thereto.

EXAMPLE 1

Effect of Pentavalent Group VA Oxides on Reaction Rate and Catalyst Stability

This example compares the carbonylation rate and catalyst stability obtained in the practice of the present invention using $Ph_3PO$ as the pentavalent Group VA oxide and compares those results to the carbonylation rate and catalyst stability obtained using no additive.

In the experiment, the autoclave previously described herein was charged with 0.5M HI, 0.7M methyl acetate (MeOAc), 5M $H_2O$ and, separately, with 1M of $Ph_3PO$. The concentration of $Ph_3PO$ to rhodium was about 227:1. After leak testing with $N_2$ and purging with CO, the reactor was heated to 175° C. at a CO pressure of 175 psig.

Next, $4.4 \times 10^{-3}$M $[H][Rh(CO)_2I_2]$ was injected into the reactor and the pressure was raised to 400 psig. The reaction was then allowed to proceed for up to about 1 hr.

The rate of acetic acid (HOAC) production was then determined by measuring the CO uptake and converting that data to moles of CO consumed. The production of acetic acid is a direct function of CO uptake and is plotted as a function of time.

The stability of the rhodium catalyst was then determined by plotting the concentration of the active rhodium species, in terms of Rh(I) mM, that remained in the reaction mixture as a function of time.

Figure 1B:
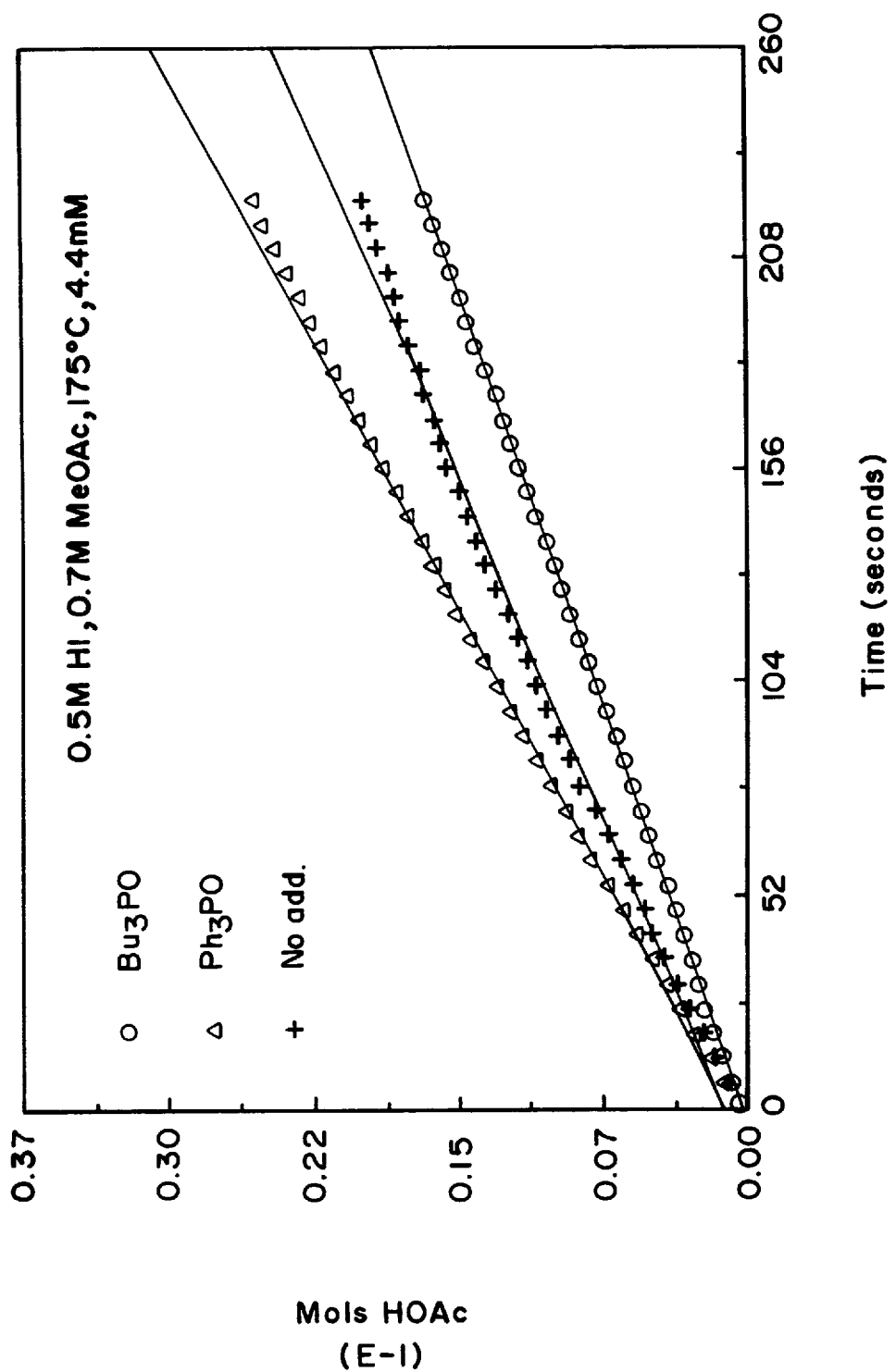
Figure 2:
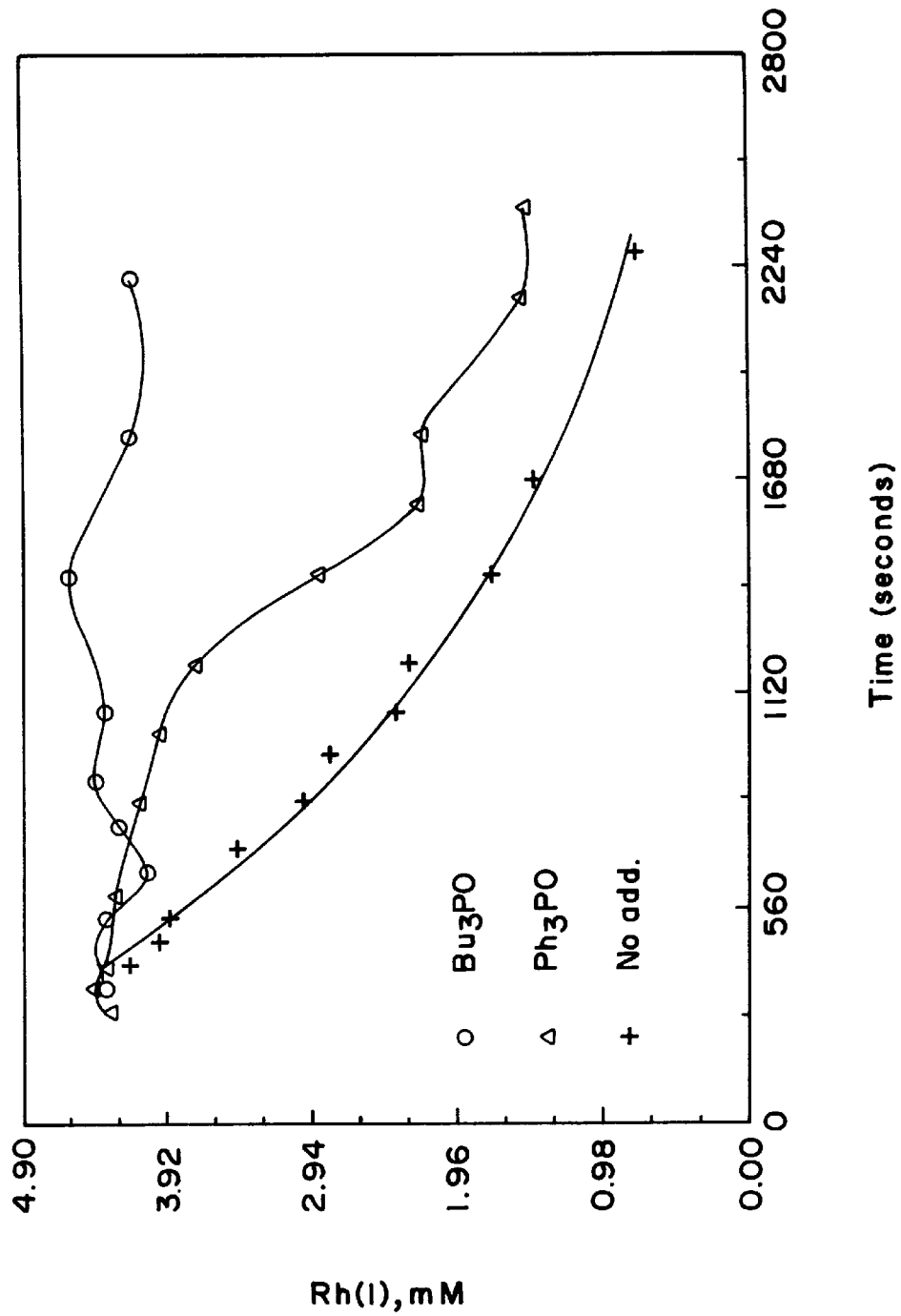
FIG. 2 is a graph showing the effect of various phosphine oxides on Rh(I) stability as exemplified in Examples 1 and 2.

The results of the foregoing experiments are shown in FIGS. 1 and 2. Specifically, as shown in FIGS. 1(a) and (b), the initial rate as well as the overall carbonylation rate was enhanced by employing $Ph_3PO$ in accordance with the present invention, as compared to the rate manifested where no additive at all was employed.

In regard to catalyst stability, FIG. 2 shows that the additive $Ph_3PO$ enhances the stability of the active Rh(I) species over a longer period of time as compared to the system wherein no additive was employed.

EXAMPLE 2

Effect of Pentavalent Group VA Oxides on Reaction Rate and Catalyst Stability

This example compares the carbonylation rate and catalyst stability obtained in the practice of the present invention using $Bu_3PO$ as the pentavalent Group VA oxide and compares those results to the carbonylation rate and catalyst stability obtained using no additive.

This experiment was conducted using the reactants and the reaction conditions set forth in Example 1 except that 1M $Bu_3PO$ was used as the additive. The concentration of $Bu_3PO$ to rhodium was also 227:1.

The results of the foregoing experiments are also shown in FIGS. 1 and 2. As is clearly shown in FIG. 1(a), an overall enhanced carbonylation rate was obtained by employing $Bu_3PO$ in accordance with the present invention, as compared to the rate manifested where no additive at all was employed.

In regard to catalyst stability, FIG. 2 shows that the additive, $Bu_3PO$, maintains catalyst stability over a much longer period of time as compared to the system wherein no additive was employed. This figure also shows that remarkably high catalyst stability can be obtained when $BU_3PO$ is used as an additive instead of $Ph_3PO$. Thus, $Bu_3PO$ is used in instances wherein high catalyst stability is required.

EXAMPLE 3

Effect of Pentavalent Group VA Oxide Levels at Low Level Water Operation

This example shows the ability of the present invention, here using $Ph_3PO$ as the pentavalent Group VA oxide, to significantly enhance the carbonylation reaction and catalyst stability at low water concentrations. Specifically in this example, three carbonylation reactions were carried out according to the protocol described in Example 1, except for the following variations:

Run 1: 3M $H_2O$; no additive
Run 2: 7M $H_2O$; no additive
Run 3: 3M $H_2O$; 1M $Ph_3PO$ The concentration of $Ph_3PO$ to rhodium was 227:1.

Figure 3A:
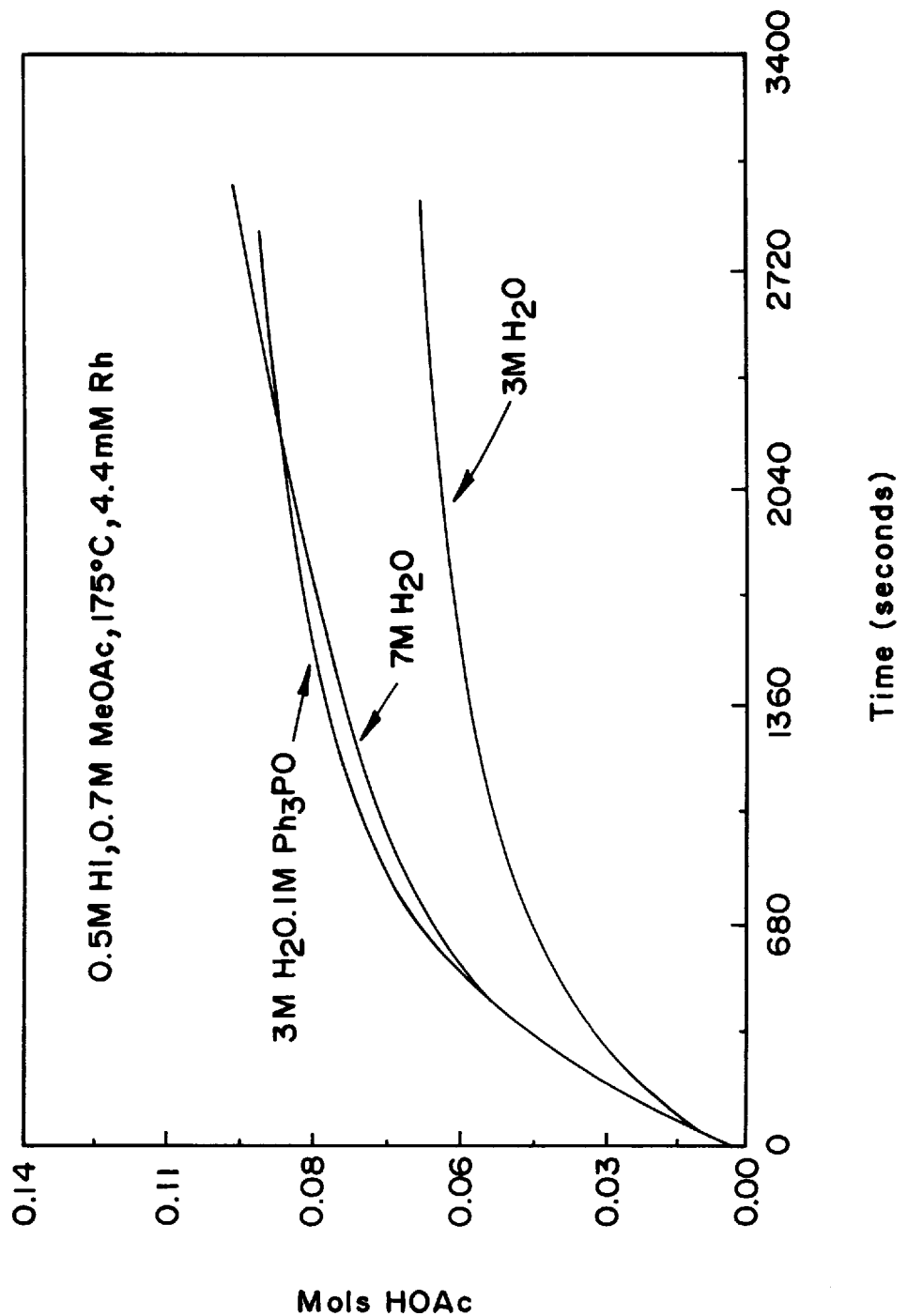
FIGS. 3(a) and (b) are graphs depicting the overall rate (a) and initial rate (b) of HOAc production at different water concentrations as exemplified in Example 3.
Figure 3B:
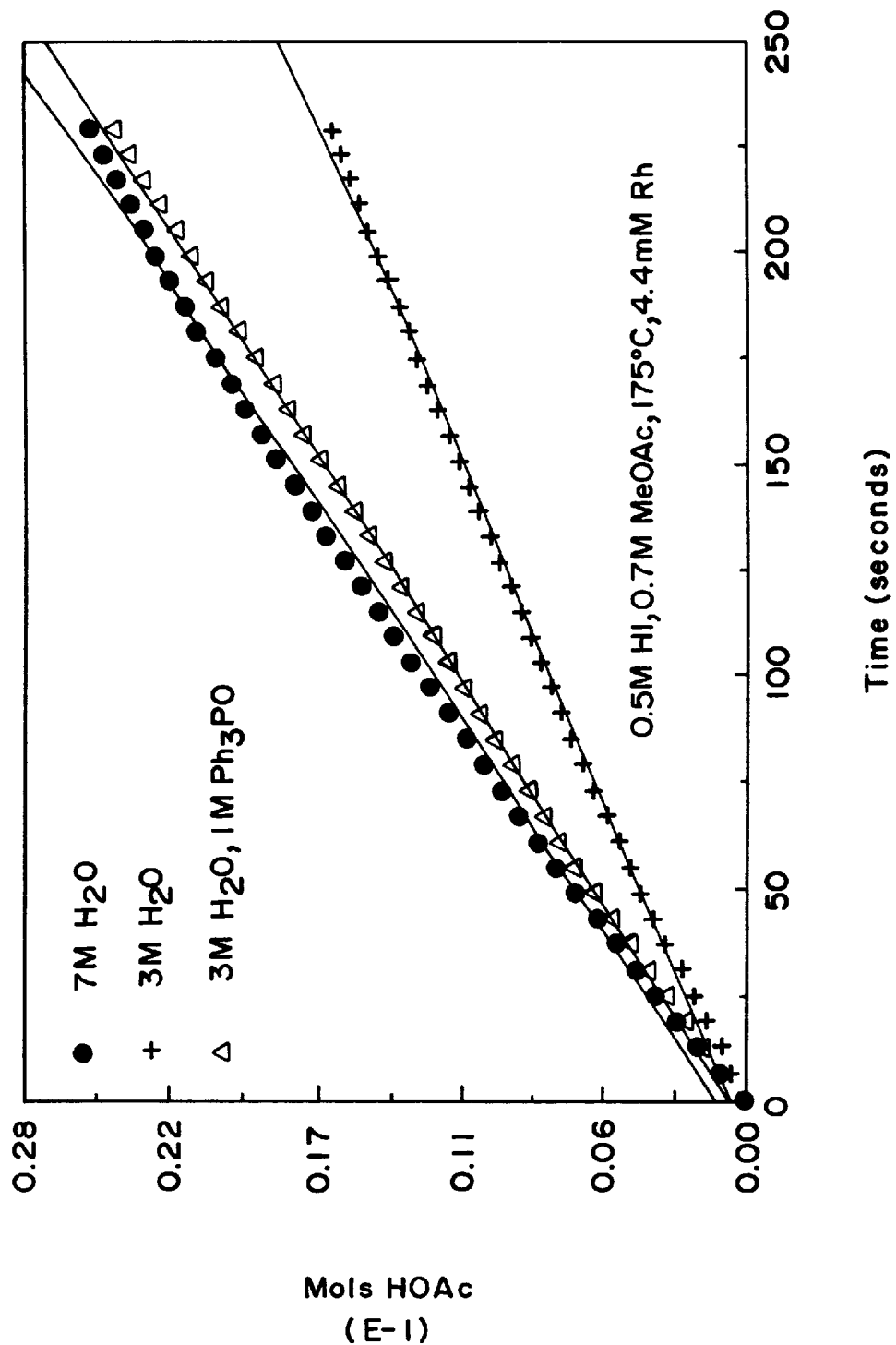

The carbonylation rates of this example are plotted in FIGS. 3(a) and (b). Specifically, the data in FIGS. 3(a) and (b) clearly show that the rate associated with a water level of 3M wherein the present invention is employed (Run 3), here using $Ph_3PO$, is commensurate with the rate observed at a water level of 7M $H_2O$ wherein no additives are employed (Run 2).

Figure 4:
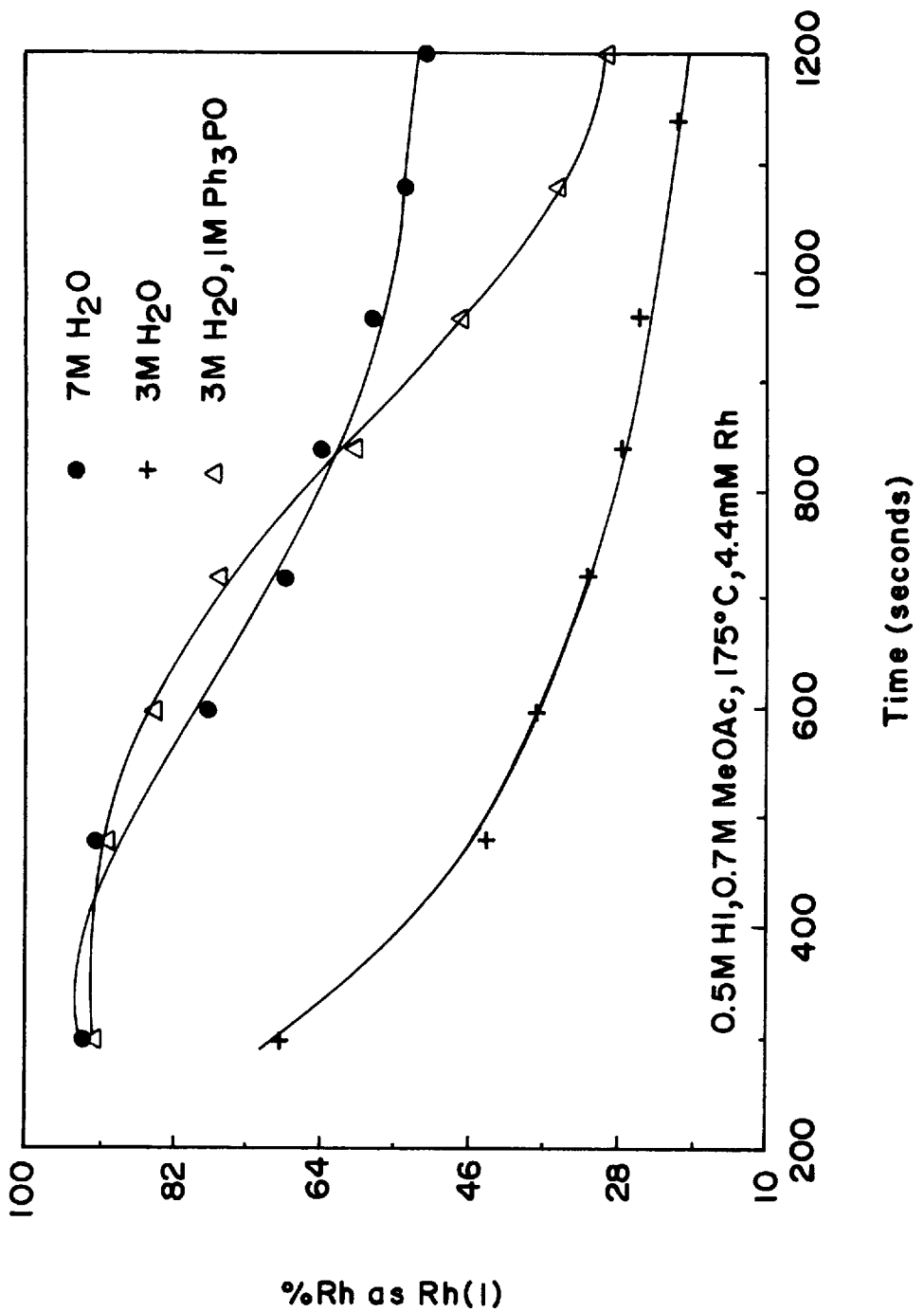
FIG. 4 is a graph showing the effect of $Ph_3PO$ on Rh(I) stability as exemplified in Example 3.

The ability to maintain catalyst stability using the above runs is plotted in FIG. 4. Specifically, this figure shows that the catalyst stability associated with a water level of 3M using $Ph_3PO$ (Run 3) as an additive is commensurate with the catalyst stability observed at a water level of 7M $H_2O$ wherein no additives are employed (Run 2). In other words, the additive of the instant invention restores the catalyst stability when operating at low water conditions; e.g. 3M, to a level which is obtained using a catalyst system wherein a higher amount of water (7M) is present.

EXAMPLE 4

Effect of % Rh as Rh(I) on Initial Rate

The experiment in Example 1 was repeated except that the following reactants, in the amounts specified below, were charged into the reactor:

MeI: 1.3M
$Ph_3PO$: 0; 0.5; 1; and 1.5M.

The respective $Ph_3PO$ to rhodium concentrations were 0; 114:1; 227:1 and 341:1.

Figure 5:
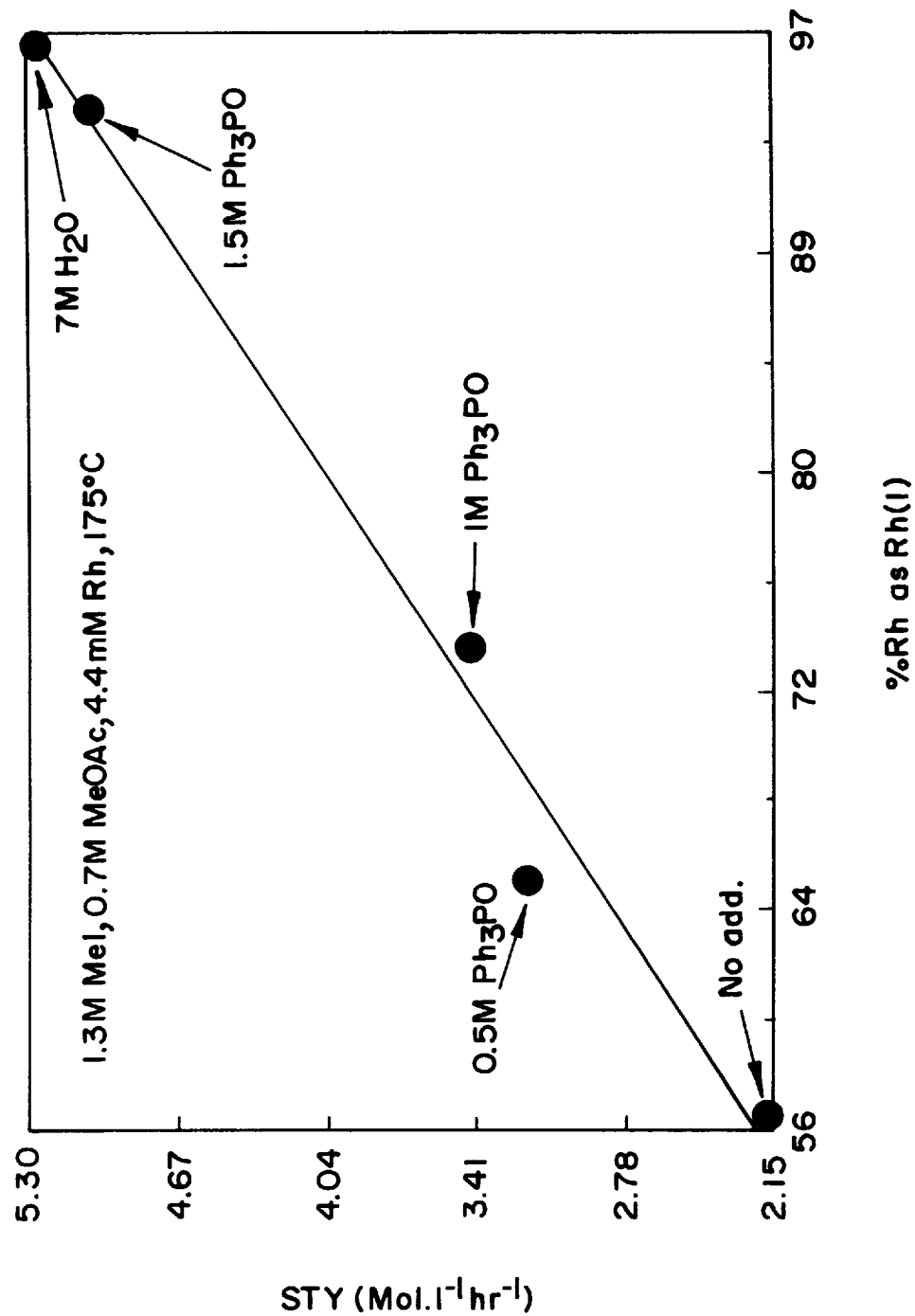
FIG. 5 is a graph of the initial rate of HOAc production, in terms of space-time-yield (STY), plotted against the % Rh as a Rh(I) species as exemplified in Example 4.

The results obtained from this experiment are plotted in FIG. 5. Specifically, the carbonylation rates, in terms of space-time-yield (STY) and expressed in moles $L^{-1}hr^{-1}$, were plotted as a function of the percent rhodium (% Rh) present as an active Rh(I) species. It is seen from this example that by increasing the concentration of $Ph_3PO$ a rate of 100% of the rate observed at 7M $H_2O$, without additives, was obtained.

EXAMPLE 5

Comparative Effects of Phosphines, Phosphites and Pentavalent Group VA Oxides on Reaction Rate and Catalyst Stability This experiment was conducted to show that in the practice of the present invention using pentavalent Group VA oxides, exemplified herein using phosphine oxides, superior reaction rate and catalyst stability resulted, as compared to the reaction rates and catalyst stability associated with the use of phosphine or phosphite additives, as known in the art. In this example, methanol carbonylation was carried out in accordance with the procedure described in Example 1 except that 3M $H_2O$ and the additives listed in the following table were charged into the reactor. The additive concentration to rhodium in each run was 227:1.

| Run No. | Additive (1M) | Type | Reaction Rate (mol/1 · hr) | Catalyst Stability % Rh as Rh (I) |
| --- | --- | --- | --- | --- |
| 1 | none | — | 1.55 | 54 |
| 2 | $Ph_3PO$ | phosphine oxide | 2.25 | 93 |
| 3 | $(PhO)_3P$ | phosphite | 0.13 | 15 |
| 4 | $(MeO)_3P$ | phosphite | 0.71 | 35 |
| 5 | $(EtO)_3P$ | phosphite | 0.15 | 30 |
| 6 | $Bu_3P$ | phosphine | 0.08 | 0 |

Figure 6:
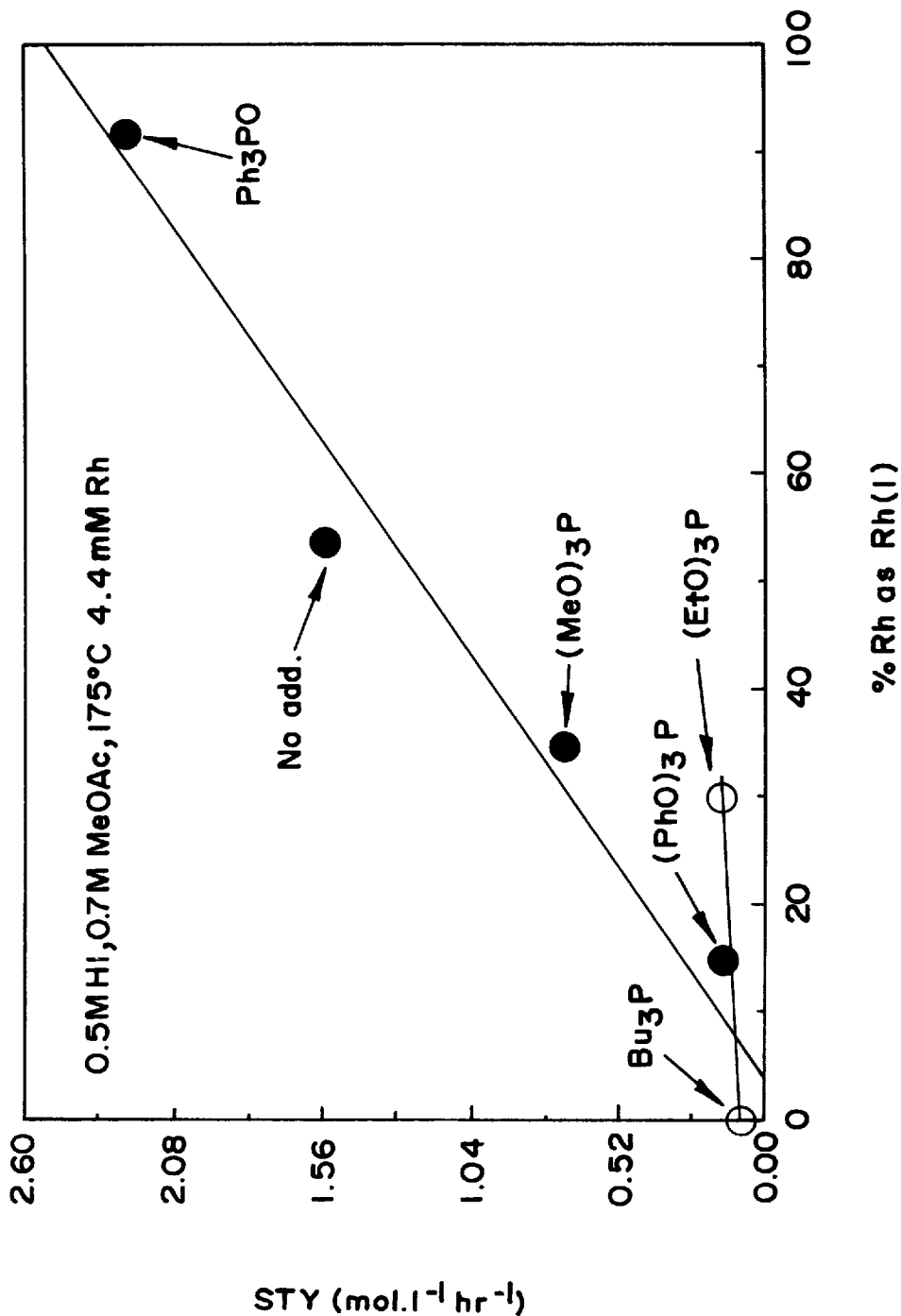
FIG. 6 is a graph showing the effect of initial Rh(I) on the initial rate of HOAc production using various phosphorus-containing additives at 3M $H_2O$ as exemplified in Example 5.

As indicated in the foregoing table and as shown in FIG. 6, the use of a phosphine oxide ($Ph_3PO$) in accordance with the present invention (Run 2) provided an unexpectedly high reaction rate and catalyst stability as compared to the system wherein no additive was employed (Run 1) or systems wherein traditional phosphites (Runs 3, 4 and 5) or a phosphine (Run 6) were employed.

EXAMPLE 6

This example attempted to reproduce the results of Example II of EP 114 703 wherein carbonylation of methanol and carbon monoxide reportedly occurred under anhydrous conditions in the presence of triphenylphosphine oxide. Next, the effect of adding water to the carbonylation process of EP 114 703 was compared with the process of the present invention. As seen from the comparison, the process of the present invention using specific levels of water in conjunction with triphenylphosphine oxide led to unexpected improvements in rate.

A. Example II of EP 114 703

All of the experiments outlined in Table B of EP 114 703 were repeated using the experimental conditions described in Example II of EP 114 703 except that CO pressure was increased from 300 psi to 400 psi and the carbonylation reaction was run for 3 hours instead of 3.5 hours. As understood to those in the art, the net effect of increasing the CO pressure in this fashion example would expectedly provide higher carbonylation rates than those reported in Table B of EP 114 703.

The results of this attempt to replicate Example II of EP 114 703 are shown in Table 1 hereinbelow. Gas chromatography was used to report the rate of acetic acid production.

As can be seen by comparing the GC rates in Table 1 to the rates reported in EP 114 703, the data at least insofar as the triphenylphosphine oxide was concerned, was not reproducible. In particular, the rates wherein triphenylphosphine oxide ($Ph_3PO$) was used were measured at far lower values than those recited in EP 114 703.

TABLE 1

| MeI (mmols) | $Ph_3PO$ (mmols) | $Ph_3P$ (mmols) | Rate measured by present Example 6 GC* qHac/ql/qRh/hr(Q) | Rate reported in EP 114 703* Table B |
|---|---|---|---|---|
| 34 | — | — | 29.1 | 27 |
| 34 | 8 | — | 39.1 | 65 |
| 17 | 8 | — | 54.6 | 70 |
| 34 | — | 8 | 40.0 | 56 |
| 34 | — | — | 39.9** | — |
| 34 | — | — | 0*** | — |

*= Gas Chromatography (MeI/MeOAc/MeOH)
**= RhOAc
***= No catalyst

B. Effect of Adding Water to the Anhydrous Carbonylation System of EP 114 703 and Comparison with the Low Water Carbonylation System of the Present Invention Water in varying amounts was next added to the anhydrous carbonylation system described in Example II of EP 114 703 (containing 8 mmol of $Ph_3PO$ and 34 mmol of $CH_3I$), the results obtained thereby were compared to the process of the present invention. Control experiments that contained no additive were also carried out. The conditions for the carbonylation reactions are the same as those described in Part A of this example.

The results are shown in Table 2 below. The Relative Rate (Rel. Rate) reported in Table 2 was calculated using the following equation:

$$Rel\ \text{Rate} = \frac{\text{Rate without additive}}{\text{Rate with additive}}$$

As can be seen from Table 2, when water at levels of from 3.1 to 7.2M was added to the process of EP 114 703, the Relative Rate was uniformly greater than 1.0. This meant that for the process described in EP 114 703, the rate obtained without the $Ph_3PO$ additive was greater than that obtained with it. There was thus no advantage gained by employing $Ph_3PO$ with these levels of water under the conditions described in the reference. Indeed, there was no substantial change in rate exhibited at all for these particular runs, the Relative Rates being 1.08 (3.1M $H_2O$), 1.03 (6.2M $H_2O$) and 1.02 (7.2M $H_2O$).

In contrast to these results is the effective increase in Relative Rate in the process of the present invention when water is added at these same levels. As seen in Table 2, when water is added at a level of 3.1M, the Relative Rate measured for the present process using $Ph_3PO$ as additive was 0.68; at 6.2M $H_2O$, it was 0.81; and at 7.2M it was 1.02. This meant that for the process of the present invention, the rate obtained with the $Ph_3PO$ additive at these water levels was greater than without it. These results are directly opposite to those shown for EP 114 703.

In view of the results tabulated in Table 2, it can be concluded that EP 114 703 does not disclose that improved carbonylation rates can be obtained using phosphine oxides within the range of water mentioned hereinabove. In fact, the data presented herein shows otherwise.

TABLE 2

| $H_2O$, M | Rel. Rate EP 114 703 | Rel. Rate Present Invention |
|---|---|---|
| 0 | 0.59 | NA |
| 1.9 | 0.76 | NA |
| 2.7 | — | 0.57 |
| 3.1 | 1.08 | 0.68 |
| 6.2 | 1.03 | 0.81 |
| 7.2 | 1.02 | 1.02 |
| 10.0 | 0.98 | 1.02 |

The above embodiments and examples are given to illustrate the scope and spirit of the present invention. These embodiments and examples will make apparent, to those skilled in the art, other embodiments and examples. These other embodiments and examples are within the contemplation of the present invention; therefore, the instant invention should be limited only by the appended claims.

What is claimed is:

1. A process for the production of acetic acid without the use of an alkali metal halide comprising contacting methanol or methyl acetate with carbon monoxide in the presence of a carbonylation system containing from about 200 to about 1200 ppm of a rhodium-containing component and a liquid reaction medium comprising from about 20 to about 80 weight % acetic acid; from about 0.6 to about 36 weight % methyl iodide; from about 0.5 to about 10 weight % methyl acetate, said contacting being in the presence of at least one pentavalent Group VA oxide of the formula $R_3M=O$, wherein M is an element of Group VA of the Periodic Table of the Elements; and each R is independently a substituted or an unsubstituted alkyl containing up to 12 carbon atoms, an aryl containing from 6 to 14 carbon atoms, an aralkyl containing up to 16 carbon atoms wherein each aryl group contains from 6 to 10 carbon atoms and each alkyl group contains up to 6 carbon atoms or an alkaryl containing up to 16 carbon atoms wherein each alkyl group contains up to 8 carbon atoms and each aryl group contains from 6 to 10 carbon atoms, wherein any of said substituents of the carbon chains may be straight, branched or both, wherein said pentavalent Group VA oxide is present in a concentration of said Group VA oxide to rhodium of greater than about 60:1, and water, said water being added in an amount of from about 4 to about 12 weight %, based on the total weight of said carbonylation system.

2. The process of claim 1 wherein said water is added in an amount of from about 4 to about 11 weight %.

3. The process of claim 2 wherein said water is added in an amount of from about 4 to about 9 weight %.

4. The process of claim 1 wherein said concentration of said pentavalent Group VA oxide to said rhodium is from about 60:1 to about 500:1.

5. The process of claim 4 wherein M is phosphorus and each R is independently a substituted or unsubstituted alkyl or aryl containing from about 1 to about 8 carbon atoms.

6. The process of claim 5 wherein at least one R is a substituted or unsubstituted phenyl.

7. The process of claim 5 wherein said pentavalent Group VA oxide is triphenylphosphine oxide or tributylphosphine oxide.

8. The process of claim 6 wherein said pentavalent Group VA oxide is triphenylphosphine oxide.

9. The process of claim 1 further comprising introducing hydrogen to said carbonylation system.

10. The process of claim 9 wherein said hydrogen is introduced in an amount sufficient to maintain a concentration of hydrogen of from about 0.1 to about 5 mole % $H_2$ in said reaction.

11. The process of claim 10 wherein said hydrogen is introduced in an amount sufficient to maintain a concentration of from about 0.5 to about 3 mole % $H_2$.

12. The process of claim 1 further comprising introducing HI to said carbonylation system.

13. The process of claim 12 wherein said HI is present in a concentration of from about 0.6 to about 23 weight %.

14. The process of claim 13 wherein said HI is present in a concentration of from about 2.3 to about 11.6 weight %.

15. The process of claim 1 further comprising an inert solvent or diluent.

16. The process of claim 15 wherein said inert solvent or diluent is 1,4-dioxane, a polyethylene glycol diether, a polyethylene glycol diester, diphenyl ether, sulfolane, toluene, a carboxylic acid and mixtures thereof.

17. The process of claim 1 wherein said rhodium-containing component is $Rh_2(CO)_4I_2$, $Rh_2(CO)_4Br_2$, $Rh_2(CO)_4Cl_2$, $Rh(CH_3CO_2)_2$, $Rh(CH_3CO_2)_3$ or $[H][Rh(CO)_2I_2]$.

18. The process of claim 1 wherein said rhodium-containing component is $[H][Rh(CO)_2I_2]$, $Rh(CH_3CO_2)_2$ or $Rh(CH_3CO_2)_3$.

19. The process of claim 1 wherein said rhodium-containing component is present in an amount of from about 400 to about 1000 ppm.

20. The process of claim 1 wherein said concentration of water is from about 2.7 to about 7M.

21. The process of claim 1 wherein said methyl acetate is present in an amount of from about 1 to about 8 weight %.

22. The process of claim 1 wherein said methyl iodide concentration is from about 3.6 to about 24 weight %.

23. The process of claim 1 wherein said acetic acid is present in an amount of from about 35 to about 65 weight %.

24. The process of claim 1 further comprising recovering acetic acid.

* * * * *